US00PP14709P2

(12) United States Plant Patent
Trees

(10) Patent No.: US PP14,709 P2
(45) Date of Patent: Apr. 20, 2004

(54) ANTIRRHINUM PLANT NAMED 'BALUMRED'

(50) Latin Name: *Antirrhinum majus*
Varietal Denomination: Balumred

(75) Inventor: Scott C. Trees, Shell Beach, CA (US)

(73) Assignee: Ball Horticultural Co., West Chicago, IL (US)

( * ) Notice: Subject to any disclaimer, the term of this patent is extended or adjusted under 35 U.S.C. 154(b) by 0 days.

(21) Appl. No.: 10/361,905

(22) Filed: Feb. 10, 2003

(51) Int. Cl.[7] ..... A01H 5/00
(52) U.S. Cl. ..... Plt./322
(58) Field of Search ..... Plt./322

*Primary Examiner*—Bruce R. Campell
*Assistant Examiner*—Anne Marie Grunberg
(74) *Attorney, Agent, or Firm*—C. A. Whealy

(57) ABSTRACT

A new and distinct cultivar of Antirrhinum plant named 'Balumred', characterized by its upright, outwardly spreading and mounded plant habit; freely basal branching growth habit; and dark red-colored flowers.

2 Drawing Sheets

Botanical classification/cultivar denomination: *Antirrhinum majus* cultivar Balumred.

BACKGROUND OF THE INVENTION

The present Invention relates to a new and distinct cultivar of Antirrhinum plant, botanically known as *Antirrhinum majus*, and hereinafter referred to by the name 'Balumred'.

The new Antirrhinum is a product of a planned breeding program conducted by the Inventor in Arroyo Grande, Calif. The objective of the breeding program is to develop new vigorous Antirrhinum cultivars that have a freely basal branching growth habit and numerous flowers with attractive coloration.

The new Impatiens originated from a cross-pollination made by the Inventor in 2000 of a proprietary selection of *Antirrhinum majus* identified as code number 59, not patented, as the female, or seed parent, with a proprietary selection of *Antirrhinum majus* identified as code number 378-1, not patented, as the male, or pollen parent. The cultivar Balumred was discovered and selected by the Inventor as a flowering plant within the progeny of the stated cross-pollination in a controlled environment in Arroyo Grande, Cailf.

Asexual reproduction of the new cultivar by cuttings taken in Arroyo Grande, Calif. since January, 2000, has shown that the unique features of this new Antirrhinum are stable and reproduced true to type in successive generations.

SUMMARY OF THE INVENTION

The following traits have been repeatedly observed and are determined to be the unique characteristics of 'Balumred'. These characteristics in combination distinguish 'Balumred' as a new and distinct Antirrhinum cultivar:

1. Upright, outwardly spreading and mounded plant habit.
2. Freely branching growth habit.
3. Dark red-colored flowers.

Plants of the new Antirrhinum differ from plants of the parent selections in plant growth habit and flower coloration.

Plants of the new Antirrhinum can be compared to plants of the cultivar Balumbreo, disclosed in U.S. Plant patent application Ser. No. 10/109,509. In side-by-side comparisons conducted in West Chicago, Ill., plants of the new Antirrhinum differed from plants of the cultivar Balumbreo in the following characteristics:

1. Plants of the new Antirrhinum were more compact than plants of the cultivar Balumbreo.
2. Plants of the new Antirrhinum had shorter leaves than plants of the cultivar Balumbreo.
3. Plants of the new Antirrhinum had more flowering branches per plant but fewer flowers per flowering branch than plants of the cultivar Balumbreo.
4. Plants of the new Antirrhinum and the cultivar Balumbreo differed in flower color.

BRIEF DESCRIPTION OF THE PHOTOGRAPHS

The accompanying colored photographs illustrate the overall appearance of the new Antirrhinum, showing the colors as true as it is reasonably possible to obtain in colored reproductions of this type. Colors in the photographs may differ from the color values cited in the detailed botanical description which accurately describe the colors of the new Antirrhinum.

The photograph on the first sheet comprises a side perspective view of a flowering plant of 'Balumred'.

The photograph on the second sheet comprises a close-up view of a typical flower of 'Balumred'.

DETAILED BOTANICAL DESCRIPTION

The cultivar Balumred has not been observed under all possible environmental conditions. The phenotype may vary somewhat with variations in environment such as temperature and light intensity without, however, any variance in genotype.

The aforementioned photographs and following observations and measurements describe plants grown in West Chicago, Ill., under commercial practice in a polycarbonate-covered greenhouse with day temperatures ranging from 18 to 24° C., night temperatures ranging from 10 to 13° C. and light levels ranging from 4,000 to 7,000 footcandles. Rooted young plants were planted in 10-cm containers and had been growing for about 15 weeks when the photographs and the description were taken.

In the following description, color references are made to The Royal Horticultural Society Colour Chart, 2001 Edition, except where general terms of ordinary dictionary significance are used.

Botanical classification: *Antirrhinum majus* cultivar Balumred.

Parentage:

*Female parent.*—Proprietary selection of *Antirrhinum majus* identified as code number 59, not patented.

*Male parent.*—Proprietary selection of *Antirrhinum majus* identified as code number 378-1, not patented.

Propagation:

*Type.*—Cuttings.

*Time to initiate roots.*—About 7 days at 18° C.

*Time to produce a rooted cutting.*—About 21 days at 18° C.

*Root description.*—Fibrous; whitish in color.

Plant description:

*General appearance.*—Upright, outwardly spreading and mounded plant habit; moderately vigorous to vigorous. Freely branching growth habit, about 13 flowering stems develop per plant.

*Plant height.*—About 18.6 cm.

*Plant diameter or spread.*—About 33.1 cm.

*Flowering stem (peduncle) length.*—About 17.1 cm.

*Flowering stem diameter.*—About 2.6 mm.

*Flowering stem internode lengh.*—About 1.8 cm.

*Flowering stem texture.*—Smooth, glabrous.

*Flowering stem color.*—143C.

*Foliage description.*—Arrangement: Opposite, simple. Leaves per flowering stem: About 14. Length: About 3.1 cm. Width: About 1 cm. Shape: Elliptic. Apex: Acute. Base: Attenuate. Margin: Entire. Texture, upper and lower surfaces: Smooth, glabrous. Venation pattern: Pinnate. Color: Upper surface: 137A; venation, 144B. Lower surface: 137C; venation, 144B. Petiole: Length: About 4 mm. Diameter: About 1 mm. Texture, upper and lower surfaces: Smooth, glabrous. Color, upper and lower surfaces: 144B.

Flower description:

*Flower type and flowering habit.*—Single bi-labiate flowers arranged on terminal racemes; flowers opposite. Usually about five open flowers per raceme. Flowers face outwardly. Flowers self-cleaning. Flowers not fragrant.

*Flower longevity.*—Flowers last about one week on the plant.

*Natural flowering season.*—Flowering is continuous from spring through autumn in West Chicago, Ill.

*Flower diameter.*—About 3.8 cm by 2.4 cm.

*Flower tube length.*—About 2.7 cm.

*Flower buds.*—Length: About 2.4 cm. Diameter: About 1.1 cm. Shape: Obovate. Color: N186D.

*Corolla.*—Shape: Broadly tubular. Lobe apices: Rounded. Lobe margin: Entire. Texture, upper and lower surfaces of lobes: Sparsely pubescent; velvety. Texture, throat: Densely pubescent. Lobe color: Upper and lower lips, upper surface: 53A. Upper and lower lips, lower surface: 72B. Palate: 53A with small area of N167B. Throat: Towards base, 72B; towards palate, 75C. Tube: N74C.

*Sepals.*—Quantity/arrangement: Five per flower; fused at base. Length: About 6 mm. Width: About 3 mm. Shape: Elliptic. Apex: Acute. Margin: Entire. Texture, upper and lower surfaces: Densely pubescent. Color, upper and lower surfaces: 143C.

*Pedicels.*—Length: About 7 mm. Diameter: About 1 mm. Strength: Strong; flexible. Angle: Acute. Texture: Densely pubescent. Color: 143C.

*Reproductive organs.*—Androecium: Stamen quantity: Four per flower. Stamen length: About 1.7 cm. Stamen color: Towards base, 77B; towards apex, 77D. Anther length: About 2 mm. Anther color: 11A. Pollen color: 13B. Gynoecium: Pistil quantity: One per flower. Pistil length: About 1.7 cm. Style length: About 1.3 cm. Style color: 72A. Stigma color: N144C. Ovary length: About 3 mm. Ovary texture: Densely pubescent. Ovary color: N144C.

*Seeds/fruits.*—Seed and fruit development has not been observed.

Disease/pest resistance: Plants of the new Antirrhinum have not been observed to be resistant to pathogens and pests common to Antirrhinum.

It is claimed:

1. A new and distinct cultivar of Antirrhinum plant named 'Balumred', as illustrated and described.

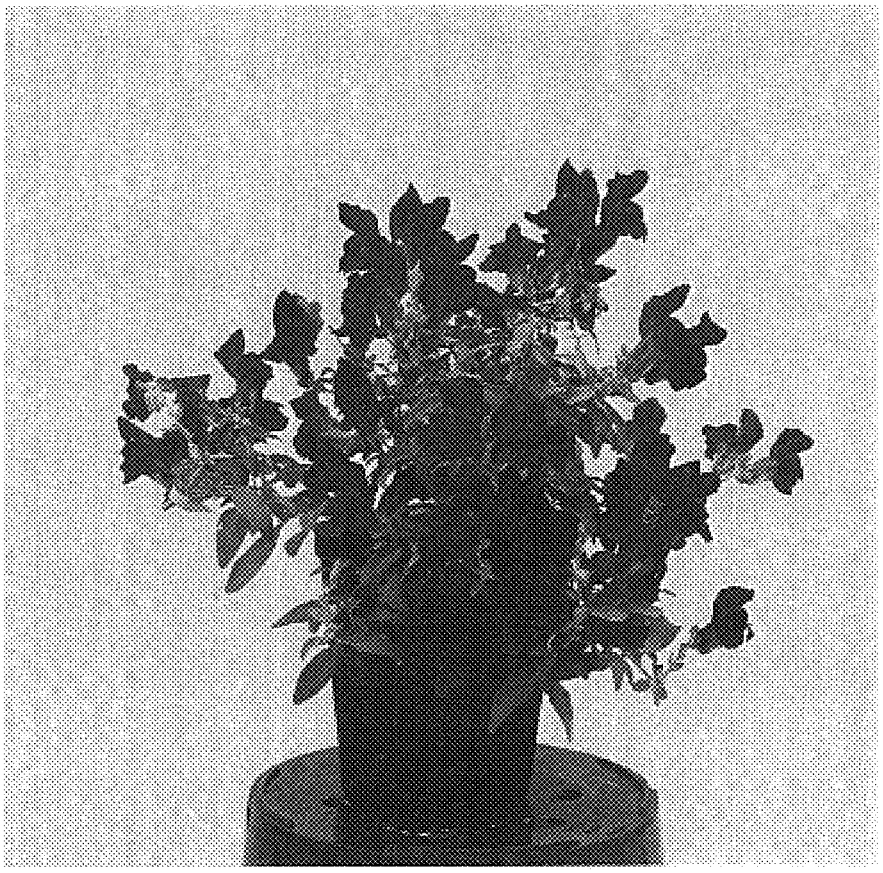

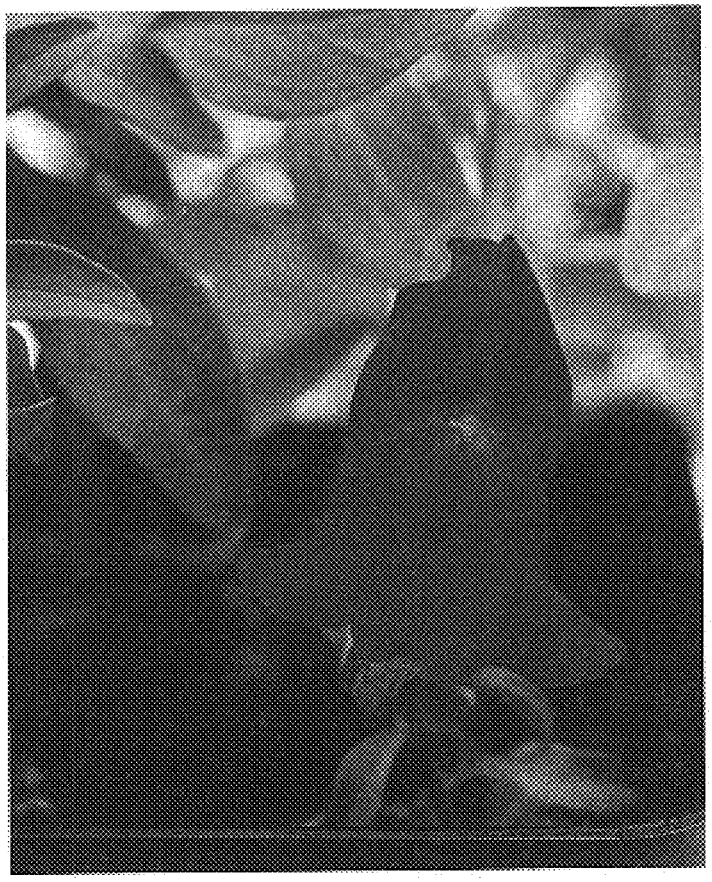

* * * * *